United States Patent [19]

Yelland

[11] Patent Number: 5,003,067

[45] Date of Patent: Mar. 26, 1991

[54] PYRIDAZINONE MANUFACTURE

[75] Inventor: Michael Yelland, Rossendale, United Kingdom

[73] Assignee: Imperial Chemical Industries PLC, London, England

[21] Appl. No.: 406,339

[22] Filed: Sep. 13, 1989

[30] Foreign Application Priority Data

Sep. 13, 1988 [GB] United Kingdom ............... 8821448

[51] Int. Cl.$^5$ ........................................ C07D 237/14
[52] U.S. Cl. ............................................ 544/239
[58] Field of Search ................................ 544/239

[56] References Cited

U.S. PATENT DOCUMENTS 4,345,934  8/1982  Fujimoto ........................... 544/239
4,623,378 11/1986  Dürr et al. ......................... 544/239
4,732,603  3/1988  Patterson ........................... 544/239

OTHER PUBLICATIONS

Patterson, Chem. Abst. 97-92301c (1982)EP 49,971.

Primary Examiner—Cecilia Shen
Attorney, Agent, or Firm—Cushman, Darby & Cushman

[57] ABSTRACT

Improved method for the manufacture of plant regulant pyridazine-4-one carboxylic acids, which comprises the step of diazo-coupling a benzenediazonium salt with a dialkyl 3-oxoglutarate in the presence of water and a dispersing agent, preferably at a temperature not greater than 5° C.

10 Claims, No Drawings

PYRIDAZINONE MANUFACTURE

This invention relates to pyridazinone manufacture, and more particularly to the manufacture of 4-pyridazinone carboxylic acids of formula (I):

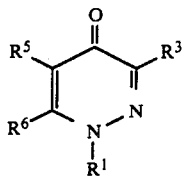

where: $R^1$ is a phenyl group, optionally substituted, with e.g. alkyl or halo groups, $R^3$ and $R^5$ are H, alkyl, halo or carboxy groups, at least one of $R^3$ and $R^5$ being carboxy; $R^6$ is H, alkyl or halo.

Compounds of formula (I) are useful as plant growth regulating compounds, and in particular as chemical hybridising agents. They have found use as male sterilants for cereal crops, for example wheat and barley, and are useful for making hybrids in such crops.

It is known from European Patent Application No. 49971 to manufacture compounds of the above formula according to the following reaction scheme.

Stage 1: Diazo-coupling

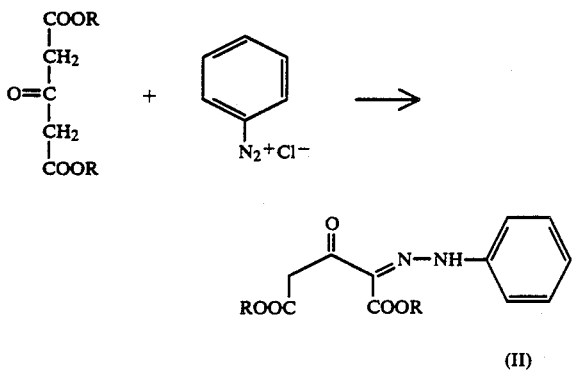

No solvent for this stage is specified, but in the Example (page 13 of 49971, A1) methanol is used as solvent, no temperature being specified.

Stage 2: Ring Closure

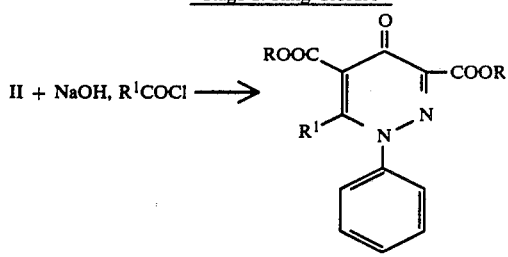

The compound (III) so obtained may then be hydrolysed either partially to the mono ester or completely to the dicarboxylic acid; and if desired, the resulting dicarboxylic acid may be partially decarboxylated. This generally gives a mixture of the two possible monocarboxylic acids, from which the desired product may be recovered.

A problem with the above process is a tendency for polychlorinated biphenyls (PCBs) to be produced in Stage 1 (diazo-coupling). This is most undesirable, as PCBs are toxic and persist in the environment: accordingly considerable care and expense must be undertaken to recover them from the reaction mixture and dispose of them safely.

We have now discovered an improved method for carrying out Stage 1 of the above reaction scheme which results in the yield of PCB byproducts being substantially reduced. According to the present invention we provide a process useful for the production of intermediates useful in the manufacture of plant-growth regulating pyridazin-4-one carboxylic acids, which comprises diazo-coupling a 3-oxoglutarate ester, particularly a dialkyl ester, with a benzenediazonium salt to give a hydrazone intermediate, characterised in that the reaction is carried out in an aqueous medium containing a dispersing agent. Preferably the temperature of the reaction is not allowed to exceed 5° C.

The benzenediazonium salt is preferably prepared in situ from a nitrite (e.g. sodium nitrite) and an aromatic amine (which may be aniline, or another amine containing further substituents, e.g. alkyl, halo or nitro groups). The dialkyl ester of 3-oxo-glutaric acid preferably is a di-(lower alkyl) ester, in which each alkyl groups contains no more than 5 carbon atoms. If desired, the diester may be unsymmetrical, containing two different alkyl groups. It is often convenient to use the diethyl ester.

The amount of water used should be at least sufficient to make the reaction mixture readily stirrable, but not so great that the mixture is unnecessarily dilute. It is usually convenient to use a mass of water in the range of 1 to 4×the total mass of all other reactants. Usually the water is acidified, e.g. with concentrated hydrochloric acid.

As dispersing agent may be used any suitable dispersant which is stabile in aqueous acid: this may include cationic, anionic or non-ionic dispersants. We prefer to use the material commercially available under the trade name "DISPERSOL" OG, a polyglycerol ricinoleate. The agent is added in amount sufficient effectively to disperse the 3-oxoglutarate ester in the water present: this is usually in the range of 0.1 to 1.0% by weight of the water in the reaction mixture.

After the reaction, the hydrazone formed may be recovered and dried. It is then conveniently subjected to the ring closure reaction outlined above to give the dicarboxylic acid diester of formula (III) above, or an analogue thereof. It may then be hydrolysed, partially decarboxylated, and formed into a salt, as desired.

Preferred chemical hybridising agents which may be produced as a final product making use of intermediates produced by the process of our invention are compounds of formula:

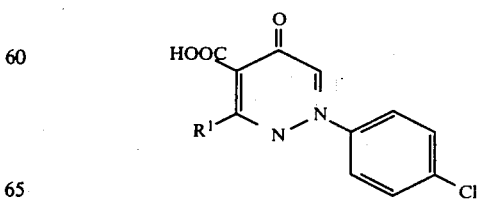

where $R^1$ is lower alkyl, especially methyl or ethyl.

The following Examples illustrate our invention:

EXAMPLE 1 p-Chloroaniline (50.3 g, 0.4 moles) was suspended in water (195 ml) containing concentrated hydrochloric acid (88 ml). The mixture was heated to 55°-60° C. to form a solution of the hydrochloride.

In a separate beaker sodium nitrite (28 g) was dissolved in water (100 ml) and ice was added to lower the temperature to 0°-2° C. The amine hydrochloride solution was then added over 15 minutes maintaining the temperature of the mixture at 0°-2° C. by the addition of ice. When the addition was complete the mixture was stirred at 0°-2° C. for 15 minutes. Excess nitrous acid was then destroyed by the addition of a 10% w/v solution of sulphamic acid. DISPERSOL OG solution (10% w/v, 12 g) was then added to the diazo suspension followed by disodium hydrogen phosphate (82.4 g). The suspension was stirred for 10 minutes at 0°-5° C. and dimethyl-3-oxoglutarate (73.4 g) was added over 1 minute. There was an exotherm at this stage but this was controlled and the temperature maintained below 5° C. by the addition of ice. The coupling mixture was stirred at 0°-5° C. for 3 hours, by which time coupling was complete. Concentrated hydrochloric acid (20 ml) was then added to lower the pH to 1.5. The product was filtered off, washed with water (31) and dried at 50° C.

The dried final product and the filtrates from the above Example were analysed by the appropriate ASTM method to determine the PCB content. This was shown to be 4.0 ppm for the solid product, and 0.22 ppm for the filtrates. This compares with figures of 23.7 ppm in the product, and 0.67 ppm in the filtrates, for a corresponding process carried out using methanol as the solvent, the temperature being maintained at or below 10° C.

I claim:

1. In a process for the manufacture of a plant-growth regulating pyridazin-4-one carboxylic acid of the formula:

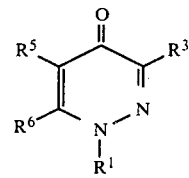

(I)

where $R^1$ is a phenyl group, $R^3$ and $R^5$ are H, alkyl, halo or carboxy groups, at least one of $R^3$ and $R^5$ being carboxy; and $R^6$ is H, alkyl or halo which includes the step of diazocoupling a 3-oxoglutarate ester with a benzenediazonium salt to give a hydrazone intermediate, which is thereafter ring-closed, the improvement whereby the reaction is carried out in an aqueous medium containing a dispersing agent which is stable in aqueous acid.

2. Process as claimed in claim 1 in which the temperature of the reaction is between 0° C. and 5° C.

3. Process as claimed in claim 1 or 2 in which the ester is a dialkyl ester in which each alkyl group contains from 1-5 carbon atoms.

4. Process as claimed in claim 3 in which the ester is the diethyl ester.

5. Process as claimed in any of claims 1-4 in which the benzenediazonium salt is prepared in situ from a nitrite and an aromatic amine.

6. Process as claimed in any of claims 1-5 in which the mass of water in the aqueous medium is in the range of 1 to 4× the total mass of all other reactants.

7. Process as claimed in any of claims 1-6 in which the aqueous medium is acidified.

8. Process as claimed in any of claims 1-7 in which the dispersing agent is polyglycerol ricinoleate.

9. Process as claimed in any of claims 1-8 in which the amount of dispersing agent is in the range of 0.1 to 1.0% by weight of the water in the reaction mixture.

10. In a process for diazocoupling a 3-oxoglutarate ester with a benzenediazonium salt to obtain a hydrazone, the improvement which comprises carrying out the reaction in an aqueous medium containing a dispersing agent which is stable in aqueous acid.

* * * * *